(12) United States Patent
Lutz

(10) Patent No.: US 11,775,061 B1
(45) Date of Patent: Oct. 3, 2023

(54) DETECTING COMPUTER INPUT BASED UPON GAZE TRACKING WITH MANUALLY TRIGGERED CONTENT ENLARGEMENT

(71) Applicant: Microsoft Technology Licensing, LLC, Redmond, WA (US)

(72) Inventor: Moshe Randall Lutz, Bellevue, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

(21) Appl. No.: 17/727,657

(22) Filed: Apr. 22, 2022

(51) Int. Cl.
*G06F 3/01* (2006.01)
*G06F 3/0481* (2022.01)
*A61B 3/113* (2006.01)

(52) U.S. Cl.
CPC .............. *G06F 3/013* (2013.01); *A61B 3/113* (2013.01); *G06F 3/0481* (2013.01)

(58) Field of Classification Search
None
See application file for complete search history.

(56) References Cited

U.S. PATENT DOCUMENTS

| 2011/0175932 A1* | 7/2011 | Yu ........................ G06F 3/04845 345/661 |
| 2014/0028549 A1 | 1/2014 | Yuan |
| 2014/0204029 A1 | 7/2014 | Lopez et al. |
| 2015/0077381 A1* | 3/2015 | Park ........................ G06F 3/013 345/174 |
| 2019/0107884 A1 | 4/2019 | Williams et al. |
| 2019/0324530 A1 | 10/2019 | Stellmach |

OTHER PUBLICATIONS

"International Search Report and Written Opinton Issued in PCT Application No. PCT/US23/012569", dated May 4, 2023, 15 Pages.

* cited by examiner

*Primary Examiner* — Christopher J Kohlman
(74) *Attorney, Agent, or Firm* — CALFEE, HALTER & GRISWOLD LLP

(57) ABSTRACT

Technologies for detecting user input based upon computed gaze of a user are described herein. With more specificity, a computing system receives an initiation command, where the initiation command indicates that the user desires to set forth input by way of gaze. Gaze points are then computed based upon images generated by a camera of the computing system; based upon such gaze points, a portion of the content is progressively enlarged. When the gaze point corresponds to a position in the content desirably selected by the user (when the portion of the content is enlarged), a selection command from the user is received. Upon receipt of the selection command, the computing system performs a computing operation with respect to the position of the content.

20 Claims, 7 Drawing Sheets

DETECTING COMPUTER INPUT BASED UPON GAZE TRACKING WITH MANUALLY TRIGGERED CONTENT ENLARGEMENT

BACKGROUND

Computer users rely on conventional input devices when interacting with a computer system, where conventional input devices include a mouse and keyboard. In an example, a computing system can receive an indication that an interactive element displayed on a display has been selected based upon input set forth to the computing system by the user through use of a mouse and/or keyboard. In another example, a computing system can detect voice input set forth by a user through use of a microphone and can identify an interactive element desirably selected by the user based upon the voice input. In still yet another example, gaze tracking technologies have been developed, where a computing system receives images from a specialized apparatus that includes a relatively high-resolution camera and depth sensor and estimates where the gaze of the user intersects with a display based upon outputs of the camera and depth sensor. Thus, the computing system can detect input set forth by the user based upon detected gaze of the user.

Conventional gaze tracking technologies have not been widely adopted, as (even with use of specialized apparatuses) conventional gaze tracking technologies are relatively inaccurate (e.g., the conventional gaze tracking technologies compute that a user is looking at a first position on the screen when the user is actually looking at a second position on the screen), resulting in user frustration. Gaze tracking technologies that utilize images from red-green-blue (RGB) cameras included within mobile telephones, laptop computers, or webcams estimate gaze locations with less accuracy than gaze tracking technologies that utilize output of specialized apparatuses, rendering conventional gaze tracking technologies unsuitable for widespread adoption. For example, content displayed on a display may include two selectable elements within close proximity to one another; output of conventional gaze tracking technologies does not allow for an operating system or application to determine which of the two interactive elements a user is attempting to select by way of gaze.

SUMMARY

The following is a brief summary of subject matter that is described in greater detail herein. This summary is not intended to be limiting as to the scope of the claims.

Described herein are various technologies related to tracking gaze of a user in connection with providing input into a computer system. In the course of a user interaction with content displayed on a display, the user may wish to select an element in the content through use of gaze. Determining, by a computing system, where a user is looking is referred to herein as gaze tracking. Use of gaze tracking to detect input to a computer system may be preferable over use of other technologies (such as a computer mouse) in certain scenarios; for example, a user who is setting forth input via a keyboard may prefer to have their hands maintain contact with the keyboard, so as to not have to remove fingers from the keyboard, use the mouse to set forth input to the computing system, and then relocate their fingers on appropriate keys of the keyboard. By tracking gaze and identifying an element that is desirably selected by the user based upon the gaze of the user, the computing system can detect selection of the element without requiring input from a computer mouse, thereby allowing the user to maintain desired positions of fingers on the keyboard The technologies described herein are employable to accurately detect input from the user by way of gaze detection, even when technologies utilized to perform gaze detection are relatively inaccurate. According to exemplary embodiments, a computing system receives an initiation command set forth by a user, where the initiation command indicates that input is to be set forth to the user by way of gaze tracking. The initiation command may comprise a keystroke on a key of a keyboard. In response to receipt of the initiation command, the computing system concurrently computes gaze points based upon images of the user generated by a camera and zooms in on a portion of content displayed on a display, where the portion of the content corresponds to the computed gaze points. The computed gaze points are indicative of locations on a display of the computing system where gaze of the user is computed to intersect the display.

With more particularity, a computed gaze point identifies a portion of the content at which the user is looking—even if the computed gaze point is inaccurate, the computed gaze point is in the general vicinity of an actual position in the content where the user is looking. Since the computed gaze point does not precisely correspond to where the user is actually looking, however, the computed gaze point may not be usable to ascertain that the user desires to set forth input with respect to a particular element included in the content, particularly when there are several elements that may be in proximity to one another. To address this issue, the computing system progressively enlarges a portion of the content based upon computed gaze points, such that, for example, elements proximate to the computed gaze points are progressively enlarged. As the computing system progressively computes gaze points and "zooms in" on the portion of the displayed content based upon the computed gaze points, a computed gaze point eventually intersects an element that is desirably selected by the user (even if the gaze point does not precisely reflect where the user is looking).

The computing system receives a selection command (e.g., a release of a keypress, a sequence of keystrokes, a voice command, etc.), which indicates that a computed gaze point is intersecting an element that is to be selected in the content. Upon receipt of the selection command, the computing system generates an indication that the user has selected the element (where the element may be a hyperlink, a button, text, an image, and so forth).

The technologies described herein exhibit various advantages over conventional technologies. As indicated previously, conventional gaze tracking technologies are not well-suited for widespread adoption due to inaccuracies in connection with estimating a gaze point in displayed content (e.g., the misalignment between where a user is actually looking and where the user is estimated to be looking). Using the technologies described herein, however, inaccuracies in computing gaze points is addressed by progressively zooming such that displayed elements proximate to computed gaze points are enlarged until an indication is received (by way of a keystroke) that a computed gaze point intersects with an element that is desirably selected by the user. In addition, the computing system can pan the content in a direction of movement of approximate gaze points over time to facilitate intersection between a graphical object and a computed gaze point.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the detailed description of the illustrated embodiments, which is to be read in connection with the accompanying drawings.

DETAILED DESCRIPTION

Figure 1:
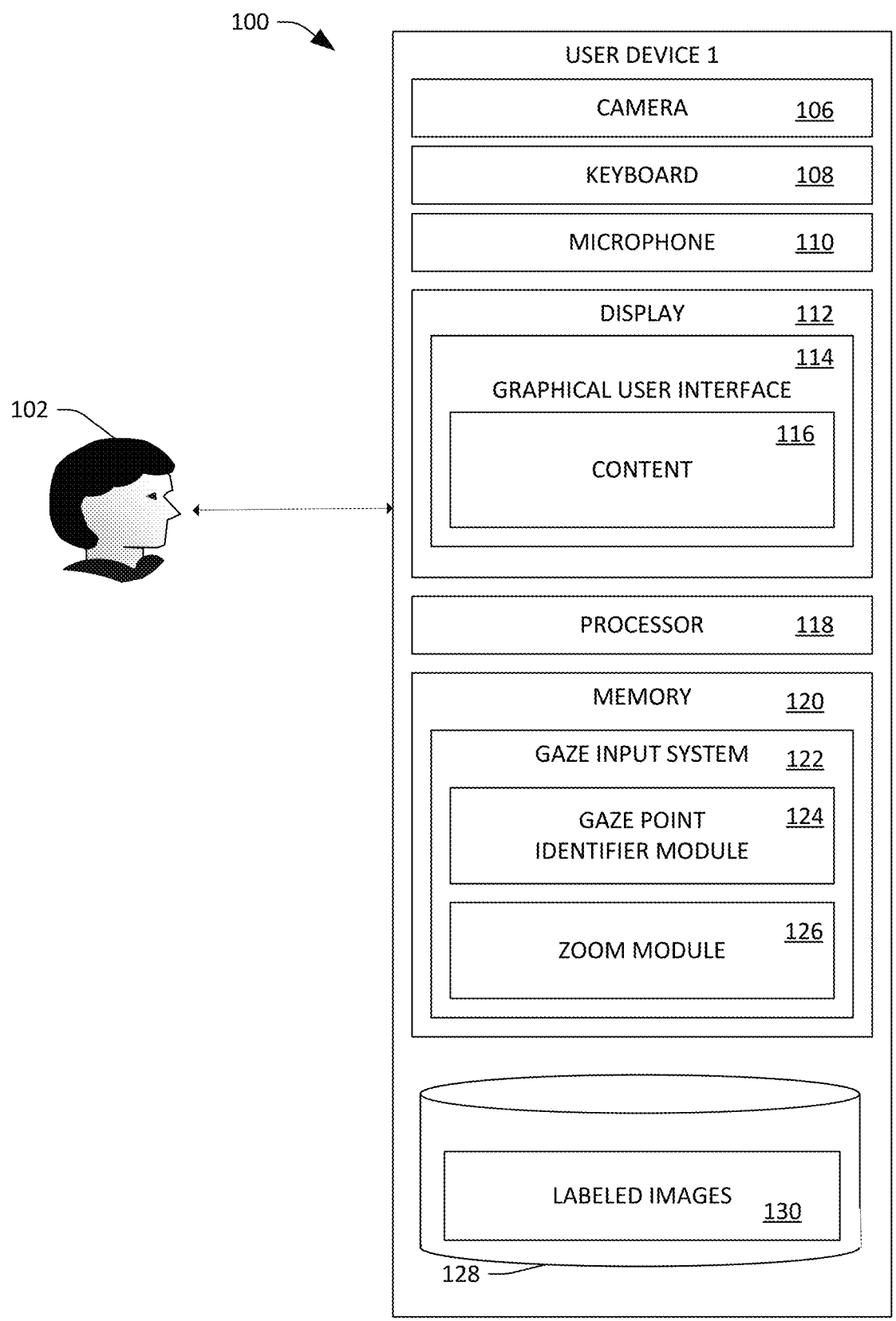
FIG. 1 illustrates a user device that is configured to identify an element that is selected by a user based upon tracking of gaze of the user.

Described herein are various technologies pertaining to altering display of content on a screen based upon computed gaze points (where the gaze points are computed based upon images generated by a camera) in connection with detecting user input with respect to a portion of content displayed on a display. In summary, a computing system receives a gaze input initiation command (e.g., a press of a key, a sequence of keystrokes, a voice command, etc.), which indicates that the user intends to interact with the content displayed on the display by way of gaze. In response to receipt of the initiation command, the computing system computes gaze points based upon images of the user output by a camera. The computed gaze points are estimates of where the user is looking on the display over time and are thus estimates as to wherein in the content the user is looking over time. Further in response to receipt of the initiation command, the computing system progressively zooms in on a portion of the content based upon the computed gaze points, such that graphical elements proximate the computed gaze points are enlarged on the display while graphical elements that are not proximate the computed gaze points may leave the display. Even when the computed gaze points are somewhat inaccurate (e.g., the computed gaze points do not precisely correspond to where the user is actually looking), as the graphical element(s) are progressively enlarged and the computed gaze points are continuously updated, a computed gaze point will eventually intersect a graphical element that is desirably selected by the user. The computing system receives a selection command (e.g., release of a keypress, a keystroke, a sequence of keystrokes, voice input, etc.), and determines a location of the computed gaze point when the selection command is received. The computing system may then pass that location to an application that is displaying the content, such that an element in the content that intersects with the gaze point is selected by the application. Hence, the computing system can identify an element that is desirably selected by a user based upon estimated gaze points (computed based upon images generated by a camera), even when the estimated gaze points are somewhat inaccurate. These aspects are described in greater detail below.

In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Further, as used herein, the term "exemplary" is intended to mean serving as an illustration or example of something and is not intended to indicate a preference.

Further, as used herein, the terms "component", "system", "module", and "model" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices.

With reference to FIG. 1, an exemplary user device 100 is illustrated. The user device 100 is configured to estimate gaze direction of a user 102 based upon images of the user 102, is configured to compute gaze points (locations on a display where the user 102 is believed to be looking) based upon the estimated gaze directions, and is further configured to perform a computing operation with respect to content displayed on a display based upon the computed gaze points. The user device 100 may be, for example, a mobile telephone, laptop or desktop computer, a table computing device, a virtual reality headset, an augmented reality headset, or the like.

The user device 100 includes or is in communication with a camera 106. The user device 100 also optionally includes at least one of a keyboard 108 or a microphone 110, and may also include or be in communication with other input mechanisms, such as a mouse, trackpad, or the like. In addition, the user device 100 includes or is in communication with a display 112, wherein a GUI 114 that depicts content 116 is presented on the display 112. The GUI 114 may be for a computer-executable application being executed by the user device 100 or for an operating system of the user device 100. While not depicted in FIG. 1, the content 116 includes elements that are selectable by the user 102, such as hyperlinks, buttons, sliders, text fields, images, etc.

The user device 100 further includes a processor 118 and memory 120, where the processor 118 executes instructions stored in the memory 120, and further where the instructions, when executed by the processor 118, cause the processor 118 to perform a routine, function, or the like. As illustrated, the memory 120 has a gaze input system 122 stored therein. As described herein, the gaze input system 122 facilitates detection of user input with respect to a position of the content 116 based upon computed gaze points, where the gaze points are indicative of location(s) on the display 112 where the user 102 is looking.

With more particularity, the gaze input system 122 includes a gaze point identifier module 124 and a zoom module 126. The gaze point identifier module 124 is configured to compute gaze points based upon images of the user 102 generated by the camera 106, where the gaze point identifier module 124 is further configured to compute the gaze points in response to receipt of a gaze initiation command from the user 102 (where such command is received by way of the keyboard 108 or microphone 110, for example). The gaze points are approximate positions on the display 112 (and thus within the content 116) where the user 102 is looking. The gaze point identifier module 124 continuously computes gaze points based upon images generated by the camera 106 as such images are received.

The zoom module 126 is configured to zoom in (and out) with respect to the content 116 based upon the gaze points computed by the gaze point identifier module 124 over time. With more particularity, when the gaze initiation command is received, the gaze point identifier module 124 is configured to compute a gaze point. The zoom module 126 can optionally be configured to pan the content 116 such that graphics in the content 116 where the gaze point intersects with the content are moved towards a center of the display 112. In addition, and as the content 116 is being panned, the zoom module 126 is configured to zoom in on the content 116, such that a portion of the content 116 proximate the computed gaze points is progressively enlarged as the gaze point identifier module 124 continues to compute gaze points. Thus, effectively, the zoom module 126 is configured to zoom in upon a portion of the content 116 being looked at by the user 102.

The gaze input system 122, subsequent to the initiation command being received, is configured to receive a selection command set forth by the user 102 by way of the keyboard 108 or microphone 110 (or optionally a mouse). Upon receipt of the selection command, the gaze input system 122 is configured to report the gaze point computed by the gaze point identifier module 124 to an application executed by the user device 100 and/or an operating system of the user device 100, and the application and/or operating system can use such gaze point as a selection input, such that an element in the content 116 at the reported gaze point is selected.

The gaze input system 122 can additionally be configured to label images generated by the camera 106, where the images are used by the gaze point identifier module 124 to compute gaze points. For example, in response to receipt of the initiation command, the gaze point identifier module 124 can compute gaze points, where a gaze point in the gaze points is computed based upon at least one image generated by the camera. As the zoom module 126 zooms in on the portion of the content 116 (or out and away from the portion of the content 116) based upon the computed gaze points, the gaze point identifier module 124 continues to compute gaze points based upon images generated by the camera 106. The gaze input system 122 assigns the computed gaze points to the images upon which the computed gaze points are based. Further, the gaze input system 122 can presume that, from the time that the initiation command was received to the time that the selection command was received, the user 102 was actually looking at the position in the content 116 that corresponds to the computed gaze point at the time that the selection command was received. Thus, for an image used by the gaze point identifier module 124 to compute a gaze point, the gaze input system 122 can assign: 1) a first label that identifies a location of the gaze point on the display 112 computed by the gaze point identifier module 124; and 2) a second label that identifies the presumed location where the user 102 was actually looking (where the presumed location is upon the computed gaze point when the selection command was received).

The user device 100 further includes a data store 128, where the data store 128 stores labeled images 130 as labeled by the gaze input system 122. As will be described below, these labeled images 130 can be used to train the gaze point identifier module 124, such that performance of the gaze point identifier module 124 is improved over time (e.g., the gaze point identifier module 124 computes gaze points with improved accuracy over time).

Exemplary operation of the user device 100 is now set forth. As described herein, the user device 100 is configured to detect a position with respect to the content 116 that has been identified by a user based upon gaze of the user 102. The camera 106 is positioned relative to the user 102 such that images generated by the camera 106 depict a face of the user 102 while the user 102 is viewing the content 116 shown on the display 112. The user device 100 receives the initiation command from the user 102 (e.g., by way of keyboard 108, microphone 110, or mouse), where the initiation command indicates that gaze of the user 102 is to be employed set forth input with respect to a portion of the content 116. In certain embodiments the initiation command is a key press (or combination of simultaneous key presses) on the keyboard 108. In other embodiments, the initiation command is sequence of key presses on the keyboard 108. In certain other embodiments, the initiation command may be a voice command or sequence of voice commands. In another example, the initiation command is a gesture.

In response to the user device 100 receiving the initiation command, the gaze point identifier module 124 computes gaze points based upon images generated by the camera 106. In the event that the camera 106 is not turned on or otherwise not ready to capture and transmit image data to the gaze input system 122, the gaze input system 122 can generate a notification for display to the user 102 (e.g., on the display 112) in order to alert the user 102 that the camera 106 is unavailable for gaze input. The gaze input system 122 may further recognize when images from camera 106 are unsuitable for computing gaze points based upon such images (e.g., due to poor lighting conditions, due to movement of the camera, etc.), and can transmit a similar notification to the user. The gaze input system 122 may alert the user 102 to take corrective action in order to allow for input to be set forth by the user 102 with respect to the content 116 based upon gaze.

As noted previously, upon receipt of the initiation command, the gaze point identifier module 124 computes gaze points based upon images generated by the camera 106. The gaze point identifier module 124 can utilize any suitable technology in connection with computing the gaze points, including image processing technologies that identify eyes of the user 102 in the images, tilt of the head of the user 102 in the images, location of pupils of the eyes of the user 102 relative to the sclera, and so forth. Further, the gaze point identifier module 124 can compute the gaze points based upon estimated location of the eyes of the user 102 relative to location and orientation of the display 112. Still further, the gaze point identifier module 124 can compute a gaze point based upon one or more previously computed gaze points. For instance, the gaze point identifier module 124 can use a smoothing function when computing gaze points, such that location of a gaze point cannot differ from a previously computed gaze point (e.g., computed immediately prior to the gaze point being computed) by more than a threshold. In another example, the gaze point identifier module 124 can compute a gaze point as being a mean of some threshold number of previously computed gaze points. Other examples of smoothing functions are also contemplated.

Further, in an example, the gaze input system 122 can cause a graphical object to overlay the content 116 to identify, to the user 102, the locations of computed gaze points. The graphical object may be crosshairs, a cursor, an arrow, or the like.

The zoom module 126 pans the content 116 and zooms in (and out) with respect to a portion of the content 116 based upon gaze points computed by the gaze point identifier module 124. For example, upon the gaze point identifier module 124 computing a gaze point, the zoom module 126 can pan the content 116 such that a portion of the content 116 that intersects the computed gaze point is moved towards a center of the display 112; in addition, the zoom module 126 zooms in upon the content 124, such that the portion of the content 116 is enlarged on the display 112. The zoom module 126 simultaneously pans and zooms the content 116 to increase a probability that a position in the content 116 that the user 102 is looking at remains displayed on the display 112 (and enlarged). The process of panning and zooming continues until: 1) the selection command is received, indicating that the gaze point is at a position in the content 116 desired by the user 102; or 2) there is a large change in gaze points over a relatively short amount of time, indicating that the gaze direction of the user 102 has changed. When the zoom module 126 determines that the gaze direction of the user 102 has changed (based upon a sequence of gaze points computed by the gaze point identifier module 124), the zoom module can pan the content 116 in the direction of the movement of the gaze direction and optionally zoom out (or cease zooming in). Thus, the zoom module 126 can pan and zoom in and out on the content 116 based upon gaze points computed by the gaze point identifier module 124. Further, upon receipt of the selection command, the zoom module 126 can zoom out so that the content 116 is displayed at the level of zoom that the content 116 was displayed at when the initiation command was received.

In another example, when a graphical indicator is not shown to identify location of a computed gaze point, upon a gaze point computed by the gaze point identifier module 124 being coincident with an element in the content 116, the gaze input system 122 can cause a visual indicator to appear with respect to the element. For instance, the element may be highlighted, change colors, etc., in a way that identifies that the computed gaze point is coincident with the element. As noted above, upon the selection command being received, the gaze input system 122 can report the computed gaze point to an application or operating system, such that the application or operating system can detect input with respect to the position in the content 116 that corresponds to a most recently computed gaze point.

After the selection command being received, the gaze input system 122 can assign labels to images used by the gaze point identifier module 124 to compute gaze points (where the images were generated by the camera 106 between when the initiation command was received and the selection command was received). As noted previously, an image can be assigned two labels: 1) a first label that is indicative of a location of a gaze point computed by the gaze point identifier module 124 based upon the image; and 2) a second label that is indicative of a location of the gaze point when the selection command was received. As will be described below, the gaze point identifier module 124 can be trained based upon labeled data generated by the gaze input system 122.

In summary, then, pursuant to an example, upon the user device 100 receiving the initiation command, the gaze input system 122 can continuously receive images from the camera 106, and the gaze point identifier module 124 can continuously compute gaze points based upon the received images, where a computed gaze point can be based upon several previously computed gaze points. Using this technique, the gaze point identifier module 124 can reduce noise that is inherent in images generated by the camera 106, as, through use of smoothing and/or weighted averaging filters (for example), the gaze point identifier module 124 can increase the signal to noise ratio of a computed gaze point (when based upon several previous gaze points) relative to the signal to noise ratio of the computed gaze point if the gaze point identifier module 124 were to compute such gaze point based solely upon a single image. In addition, the zoom module 126 further reduces noise with respect to content that is being looked at by the user, as zooming decreases scale of the noise by effectively increasing size of pixels.

Exemplary operation of the user device 100 may be further illustrated in the following examples. In one embodiment, different initiation commands or additional keystrokes used in conjunction with the initiation commands are used for different types of elements within the content 116. As an example, where selection of [key] is an initiation command, the user 102 presses Shift+[key] to indicate that the element in the content 116 that is desirably selected is a button. Buttons in the content 116 may be encoded differently from other types of elements. The gaze input system 122 can leverage this information to identify the buttons within the content 116 and therefore limit which elements are selectable by the user 102. In another example, the user 102 can press Ctrl+[key] to indicate that user 102 intends to insert a cursor for typing in the content 116 at a computed gaze point.

As yet another example, the gaze input system 122 can be used in connection with other accessibility input features such as a virtual touch keyboard. In embodiments where touch input is accepted, a virtual keyboard may be brought on screen. Just as with the user-selectable elements in a GUI, the elements of the virtual keyboard are interacted with gaze using the gaze input system 122. As elements of the virtual keyboard are enlarged based on the approximate gaze point, the accuracy of the touch input is improved.

In still yet another example, when the content 116 includes multiple selectable elements, the gaze input system 122 can move the elements away from one another. Doing so may improve the ability of the gaze input system 122 to disambiguate which element in the elements is desirably selected by the user 102 by way of gaze.

Figure 2A:
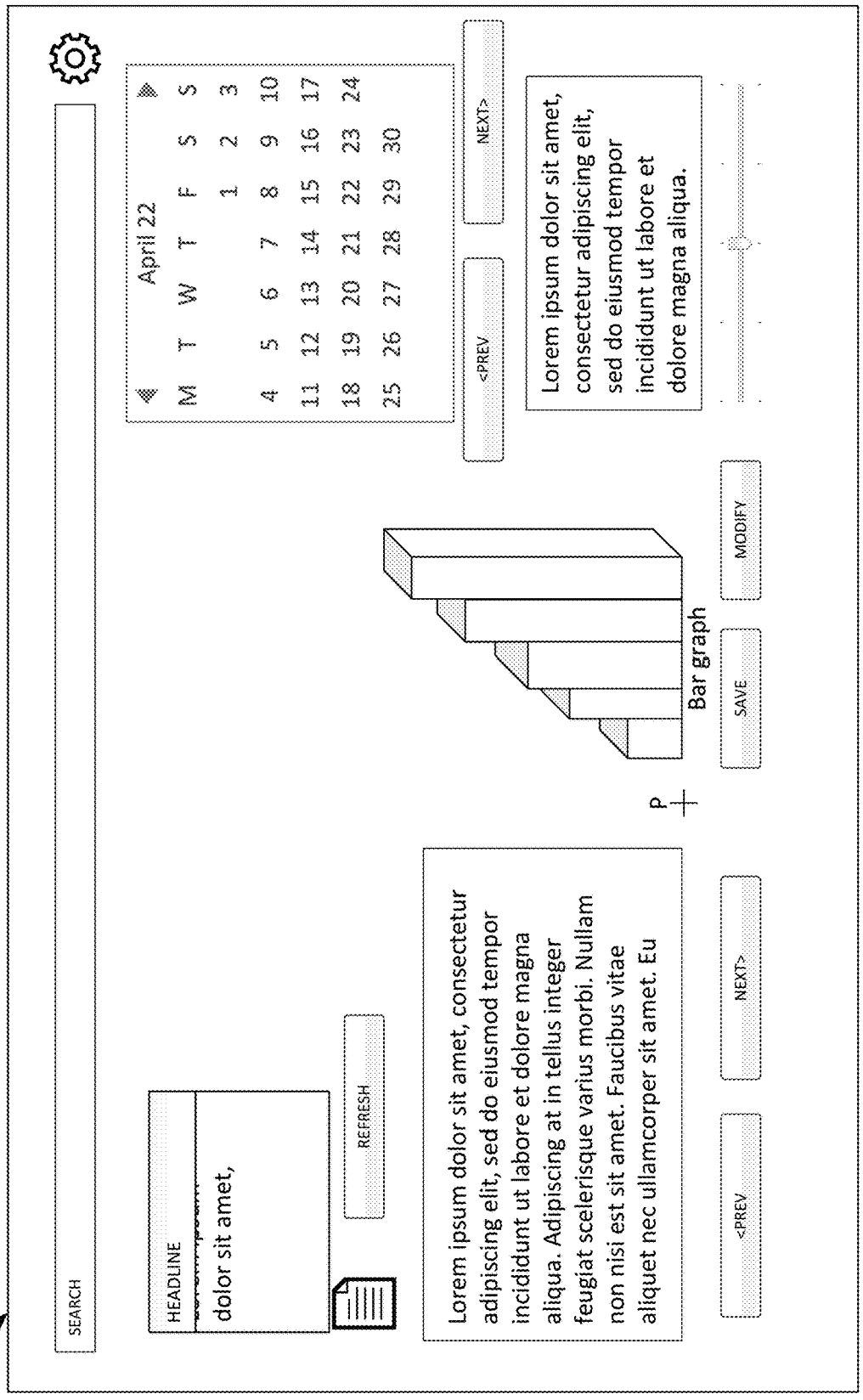
FIG. 2A illustrates a first view of content displayed upon a display when gaze input has been activated by way of an initiation command.
Figure 2B:
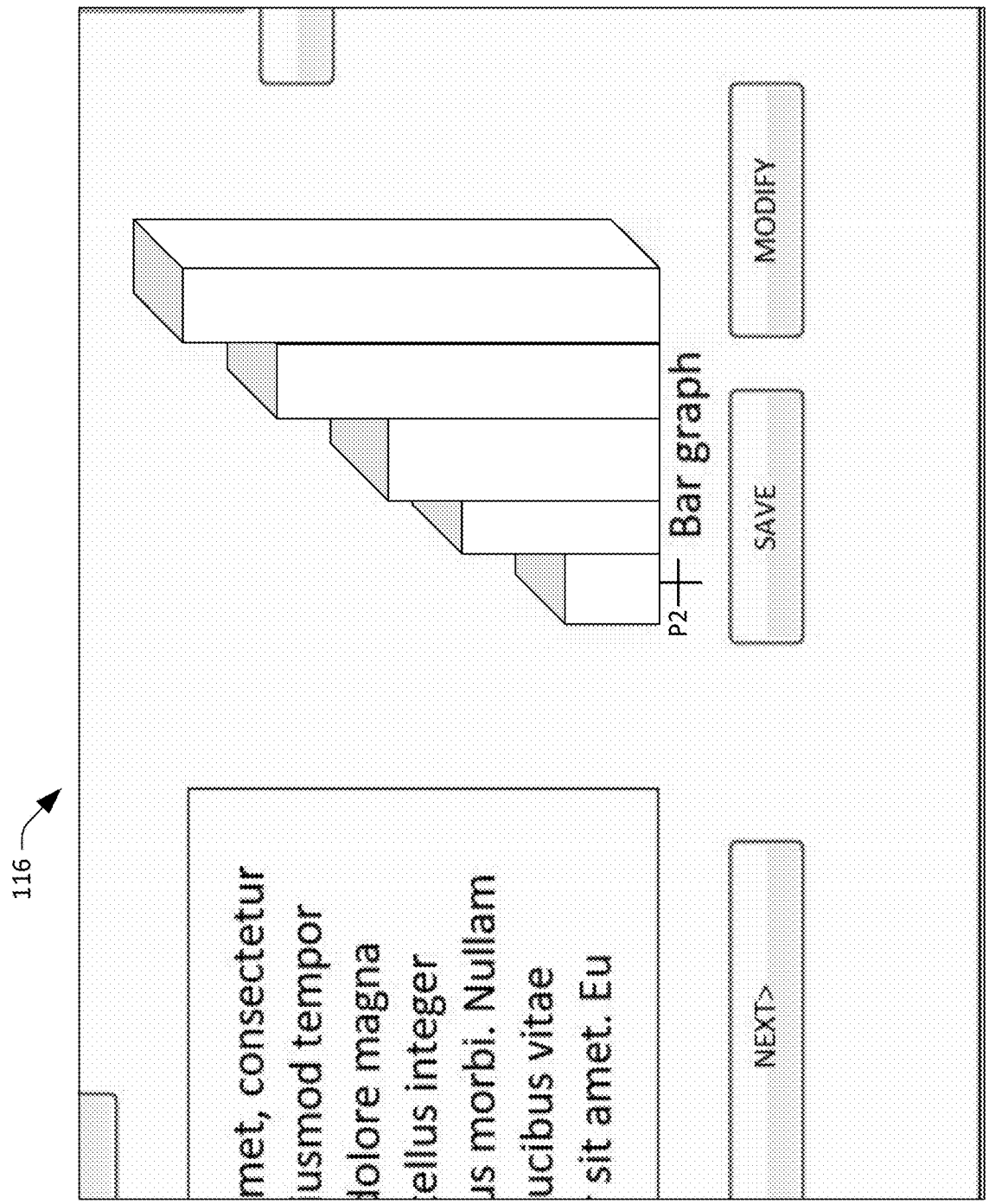
FIG. 2B illustrates a view of an enlarged portion of the content after gaze input has been activated by way of the initiation command.
Figure 2C:
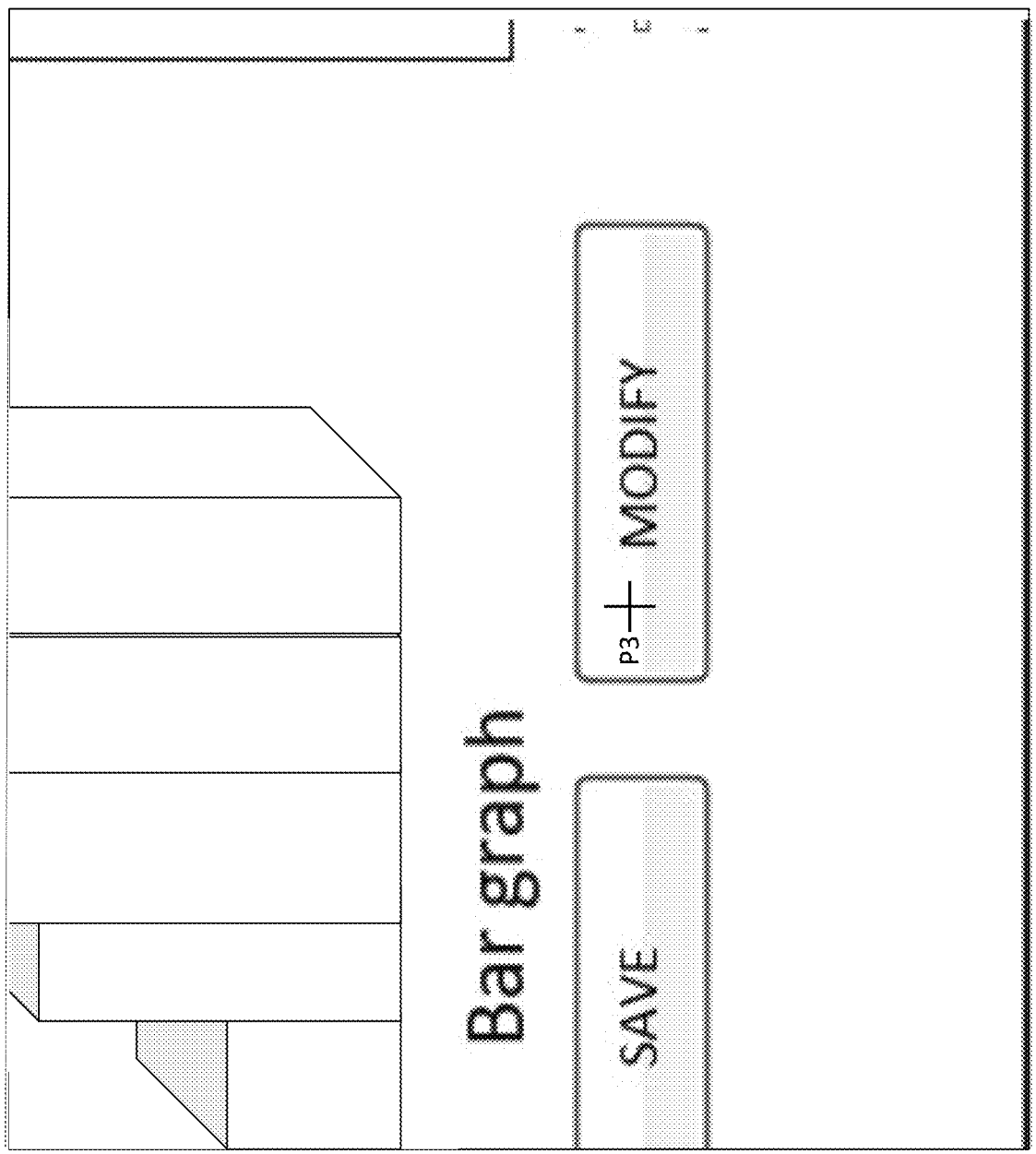
FIG. 2C illustrates a view of a further enlarged portion of the content that corresponds to when a selection command has been received indicating that an element is to be selected.

FIGS. 2A-2C illustrate exemplary views of content as the gaze point identifier module 124 computes gaze points and the zoom module 126 pans and zooms in upon a portion of the content.

FIG. 2A illustrates the content 116 having several user-selectable elements. The gaze input system 122 has received an initiation command and is receiving images from the camera 106. The gaze point identifier module 124 computes a gaze point P. In the example shown in FIG. 2A, the gaze point P may be the first gaze point computed by the gaze point identifier module 124 upon the gaze input system 122 receiving the initiation command.

FIG. 2B illustrates the content 116 after the zoom module 126 has panned the content 116 upwards and has zoomed in on a portion of the content 116, such that several elements in the content 116 are enlarged on the display 112. Additionally, the gaze point identifier module 124 has computed an updated gaze point P2 based upon at least one image output by the camera 106 as the user 102 continues to look at the display 112.

FIG. 2C illustrates the content 116 upon the zoom module 126 further panning the content 116 based upon gaze points computed by the gaze point identifier module and further zooming in on the portion of the content 116, such that elements proximate to where the user 102 is actually looking are further enlarged. As illustrated, the gaze point identifier module 124 has computed a gaze point P3, which is shown as being incident upon a graphical element (a button labeled "modify"). In this example, zooming in on the portion of the content 116 until the computed gaze point P3 unambiguously is incident upon a button desirably selected by the user 102 allows the user to select such button by setting forth the selection command. Upon receipt of the selection command, the gaze input system 122 reports the location of gaze point P3 to the application or operating system that presents the content 116, thereby indicating to the application or operating system that the button has been selected by the user 102. In another embodiment, the application or operating system can expose information about the elements to the gaze input system 122, and the gaze input system 122 can cause an element (e.g., the button depicted in FIG. 2C) to be highlighted upon the computed gaze point P3 being incident upon the button. In response to receipt of the selection command, the gaze input system 122 can indicate to the application or operating system that the element has been selected (rather than reporting a position of the selection).

Figure 3:
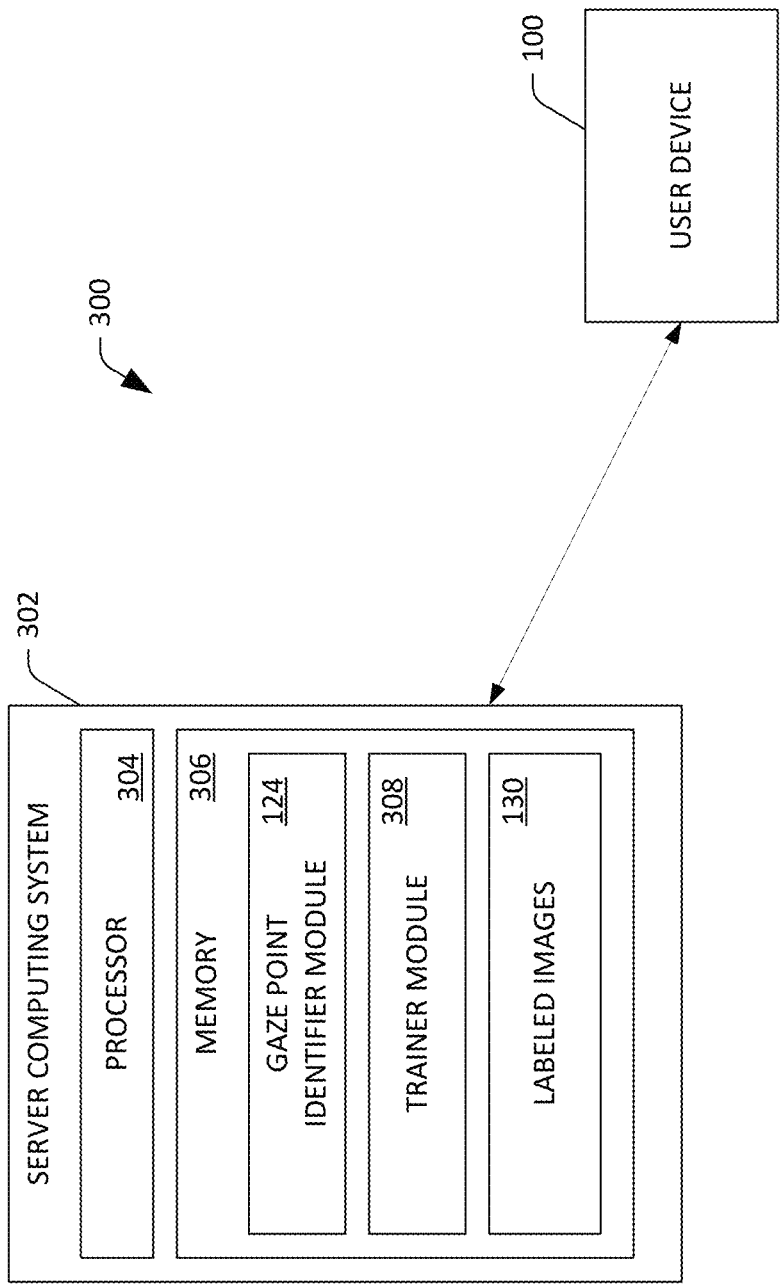
FIG. 3 is a functional block diagram of a computing system that is configured to train a computer-implemented model that is used for gaze tracking.

FIG. 3 is a functional block diagram of a computing system 300 that is configured for use in connection with training the gaze point identifier module 124. The system 300 includes a server computing system 302 and the user device 100, where the server computing system 302 is in network communication with the user device 100. As described above with respect to FIG. 1, the user device 100 can generate labeled images based upon use of the gaze input system 122. The server computing system 300 includes a processor 304 and memory 306, where the memory 306 includes modules that are executed by the processor 304 and data that can be processed by the processor 304. As illustrated in FIG. 3, the server computing system 302 includes an instance of the gaze point identifier module 124. In an example, the gaze point identifier module 124 can be or include a computer-implemented model, such as a neural network. For instance, the neural network is a deep neural network (DNN), a recurrent neural network (RNN), a convolutional neural network (CNN), a Long Short-Term Memory (LSTM) network, and so forth.

The memory 306 also includes a trainer module 308 that trains the computer-implemented model of the gaze point identifier module 124 based upon the labeled images 130 generated by the user device 100. For instance, from time to time the user device 100 can transmit labeled images to the server computing system 302, and the trainer module 308 can train the gaze point identifier module 126 based upon such labeled images. For example, the trainer module 308 can train the gaze point identifier module 126 such that loss output by a loss function is minimized (e.g., overall distance between gaze points computed by the gaze point identifier module 126 and selected gaze points by the user is minimized). The trainer module 308 can utilize any suitable training technique in connection with training the computer-implemented model, including gradient descent, conjugate gradient, or other suitable technique. Upon the computer-implemented model of the gaze point identifier module 124 being trained, the server computing system 302 can transmit the gaze point identifier module 124 to the user device 100; hence, the gaze point identifier module 124 can be constantly improved.

While FIG. 3 illustrates the gaze point identifier module 124 being updated based upon the labeled images 130 from the user device 100, it is to be understood that labeled images can be received from numerous user devices. Thus, the gaze point identifier module 124 can be trained based upon labeled images from multiple different user devices.

Figure 4:
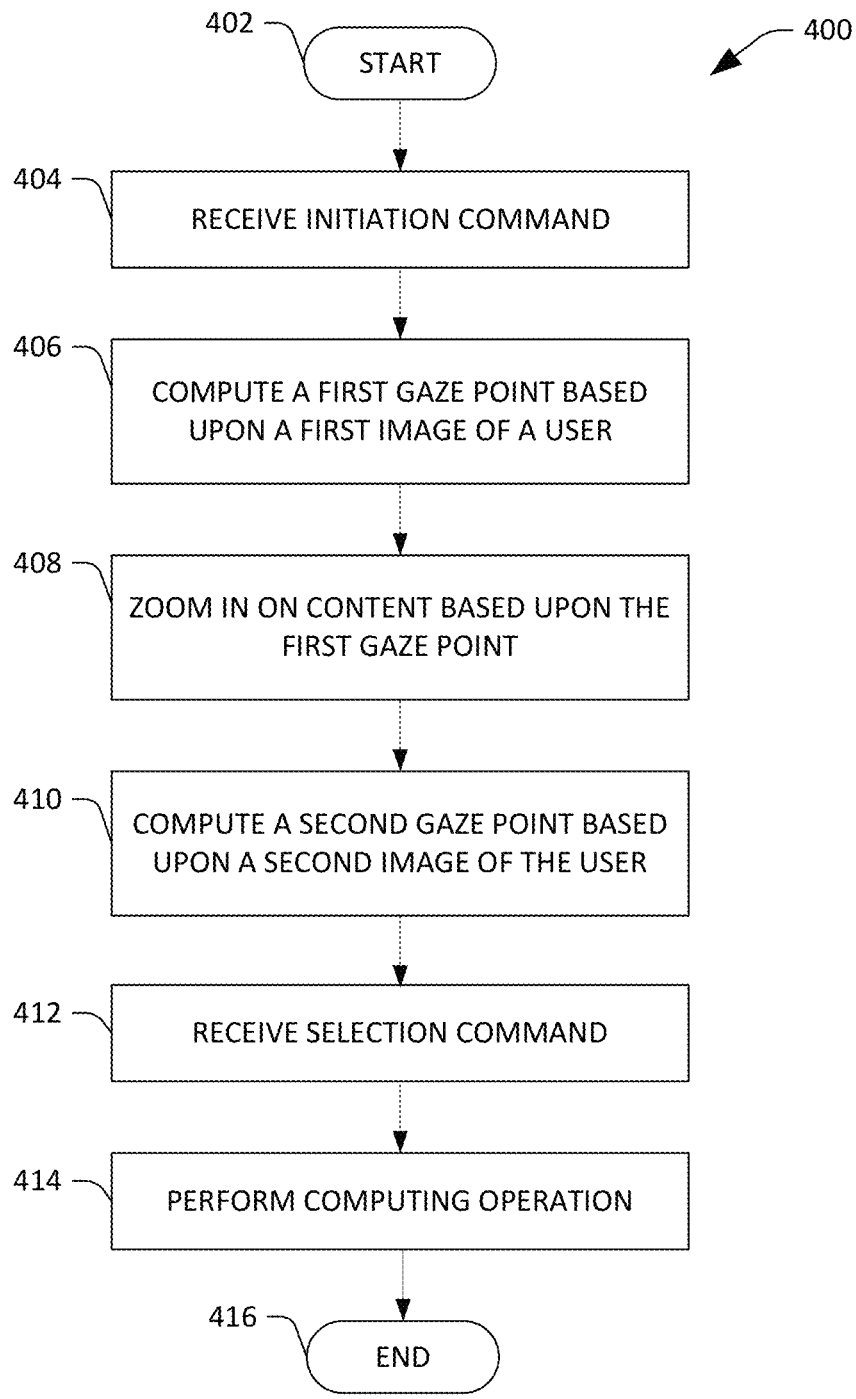
FIG. 4 illustrates a method for performing a computing operation based upon computed gaze points.

FIG. 4 illustrates an exemplary methodology 400 relating to performing a computing operation based upon gaze of a user. While the methodology 400 is shown and described as being a series of acts that are performed in a sequence, it is to be understood and appreciated that the methodology is not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodology can be stored in a computer-readable medium, displayed on a display device, and/or the like.

The methodology 400 begins at 402, and at 404, an initiation command is received, where the initiation command indicates that a computing system is to receive input from a user of the computing system with respect to content displayed on a display of the computing system, and further where the input is to be received based upon gaze of the user. As an example, the initiation command may be a press of a key of a keyboard, a sequence of keystrokes, a voice command, a gesture, or the like.

At 406, based upon receipt of the initiation command, a first gaze point is computed based upon a first image of the user generated by a camera of the computing system. The first gaze point corresponds to a first position in the content where the gaze of the user is computed to intersect with the display. For example, the content may be a webpage, a spreadsheet, a word processing document, a slide presentation document, editable source being reviewed by a developer, etc. The gaze point can be computed as an (X, Y) coordinate on the display, and can optionally be converted into a coordinate system of the content. The camera may be an RGB camera found in a commercial, off-the shelf computing device. In an example, the first gaze point can additionally be computed based upon first output of a depth sensor.

At 408, the content displayed on the display is zoomed in on based upon the first gaze point. Put differently, a portion of the content that surrounds the first gaze point is enlarged on the display (while other portions of the content may be removed from the display due to the zooming in on the content). Also, optionally, the content can be panned based upon the first gaze point. For example, when the first gaze point is on a left-hand portion of the display, the content can be panned rightward (while the content is being zoomed) such that the portion of the content corresponding to the first gaze point is moved towards a center of the display.

At 410, subsequent to zooming in on the content, a second gaze point is computed based upon a second image of the user generated by the camera of the computing system. Optionally, the second gaze point is computed based upon second output of the depth sensor. The second image is generated by the second camera subsequent to the second camera generating the first image. Additionally, the second gaze point corresponds to a second position on the content (that is different from the first position on the content) where the gaze of the user is computed to intersect with the display, where the second gaze point is computed while the portion of the content is enlarged.

At 412, subsequent to receiving the initiation command (and further subsequent to computing the first gaze point, zooming in on the content, and computing the second gaze point), receiving a selection command. The selection command indicates that a computing operation is to be performed with respect to the second position on the content. In an example, the selection command may be release of the press of the key. In another example, the selection command may be a keystroke or a sequence of keystrokes. In yet another example, the selection command may be a voice command. At 414, the computing operation is performed.

In a non-limiting example, the content may be a webpage, and the second position on the content may be a hyperlink. Thus, when the selection command is received, the hyperlink on the webpage can be selected. In such an example, the computing operation is selection of the hyperlink. In another example, the content may be a word processing document, and the second position on the content may be a particular position in the word processing document. Therefore, when the selection command is received, a cursor can be placed at the second position in the word processing document. In such an example, the computing operation is placement of the cursor in the word processing document. The technologies described herein allow for relatively inaccurate gaze tracking technology to be employed while allowing a user to accurately select an element in content displayed on a display and/or accurately place a cursor in a word processing document. The methodology 400 completes at 416.

Figure 5:
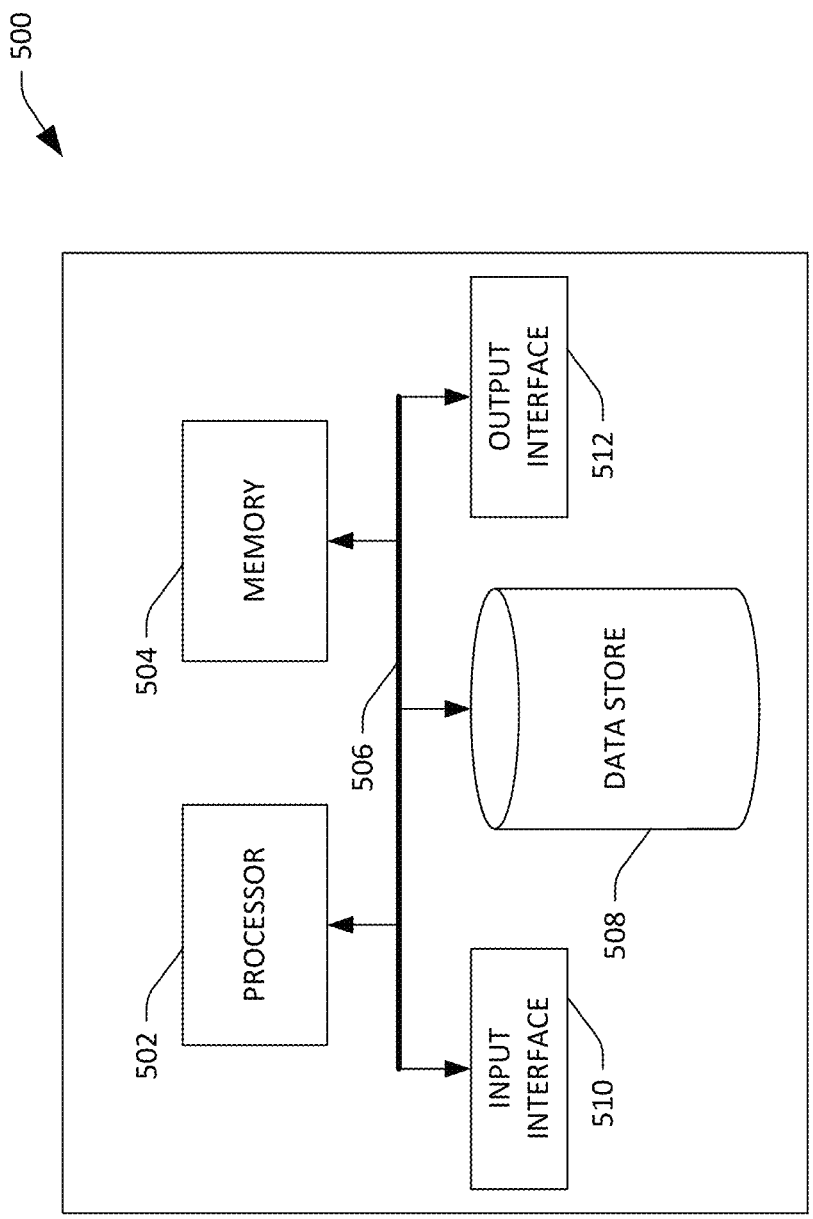
FIG. 5 illustrates an exemplary computing device.

Referring now to FIG. 5, a high-level illustration of an example computing device 500 that can be used in accordance with the systems and methodologies disclosed herein is illustrated. It is appreciated that user device 100 is one exemplary implementation of computing device 500. For instance, the computing device 500 may be used in a system that captures computer-readable user input by way of gaze tracking. The computing device 500 includes at least one processor 502 that executes instructions that are stored in a memory 504. The instructions may be, for instance, instructions for implementing functionality described as being carried out by one or more components discussed above or instructions for implementing one or more of the methods described above. The processor 502 may access the memory 504 by way of a system bus 506.

The computing device 500 additionally includes a data store 508 that is accessible by the processor 502 by way of the system bus 506. The data store 508 may include executable instructions, images, labeled images, depth values, etc. The computing device 500 also includes an input interface 510 that allows external devices to communicate with the computing device 500. For instance, the input interface 510 may be used to receive instructions from an external computer device, from a user, etc. The computing device 500 also includes an output interface 512 that interfaces the computing device 500 with one or more external devices. For example, the computing device 500 may display text, images, etc. by way of the output interface 512.

It is contemplated that the external devices that communicate with the computing device 500 via the input interface 510 and the output interface 512 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 500 in a manner free from constraints imposed by input devices such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 500 may be a distributed system. Thus, for instance, several devices may be in communication by way of a network connection and may collectively perform tasks described as being performed by the computing device 500.

The disclosure relates to performing a computer-implemented operation based upon detected gaze of a user according to at least the following examples.

(A1) In one aspect, some embodiments include a computer-implemented method performed by at least one processor of a computing system. The method includes receiving an initiation command, the initiation command indicating that the computing system is to receive input from a user of the computing system with respect to content displayed on a display of the computing system based upon a gaze of the user. The method also includes several acts that are based upon receipt of the initiation command. These acts include computing a first gaze point based upon a first image of the user generated by a camera of the computing system, wherein the first gaze point corresponds to a first position in the content where the gaze of the user is computed to intersect with the display. These acts also include zooming in on a portion of the content displayed on the display based upon the first gaze point. The acts further include, subsequent to zooming in on the portion of the content, computing a second gaze point based upon a second image of the user generated by the camera of the computing system, where the second image of the user was generated by the camera subsequent to the first image being generated by the camera, and further where the second gaze point corresponds to a second position in the content where the gaze of the user is computed to intersect with the display. The method also includes, subsequent to receiving the initiation command, receiving a selection command, wherein the selection command indicates that a computing operation is to be performed with respect to the second position in the content, and further wherein the computing operation is performed in response to receipt of the selection command.

(A2) In some embodiments of the method of (A1), the first gaze point is displaced from a center of the display, and the method also includes, while zooming in on the portion of the content displayed on the display, panning the content based upon the first gaze point, wherein the content is panned such that the first position in the content is moved towards the center of the display.

(A3) In some embodiments of at least one of the methods of (A1)-(A2), the method also includes computing a sequence of gaze points based upon a sequence of images generated by the camera, wherein the sequence of gaze points is computed subsequent to the first gaze point being computed and prior to the second gaze point being computed, wherein zooming in on the content is based upon the sequence of gaze points.

(A4) In some embodiments of at least one of the methods of (A1)-(A3), the method also includes displaying a graphical object as an overlay on the content, the graphical object is displayed at the first position based upon the first gaze point and is subsequently displayed at the second position based upon the second gaze point.

(A5) In some embodiments of at least one of the methods of (A1)-(A4), the second gaze point is computed based further upon the first gaze point.

(A6) In some embodiments of at least one of the methods of (A1)-(A5), the method also includes, subsequent to zooming in on the portion of the content and prior to computing the second gaze point, computing a third gaze point based upon a third image generated by the camera, where the third gaze point corresponds to a third position in the content where the gaze of the user is computed to intersect with the display. The method also includes zooming out from the content based upon the third gaze point.

(A7) In some embodiments of the method of (A6), the content is zoomed out from based upon a distance between the first gaze point and the third gaze point.

(A8) In some embodiments of at least one of the methods of (A1)-(A5), the method also includes, subsequent to zooming in on the portion of the content and prior to computing the second gaze point, computing a third gaze point based upon a third image generated by the camera, wherein the third gaze point corresponds to a third position in the content where the gaze of the user is computed to intersect with the display. The method also includes panning the content based upon the third gaze point.

(A9) In some embodiments of at least one of the methods of (A1)-(A8), the method also includes, in response to receiving the selection command, providing the second gaze point to an application that is displaying the content, wherein the application performs the computing operation based upon the second gaze point.

(A10) In some embodiments of the method of (A9), the computing operation is a selection of a graphical object in the content, wherein the graphical object corresponds to the second gaze point.

(A11) In some embodiments of the method of (A9), the computing operation is placement of a cursor in a text entry field in the content, wherein the text entry field corresponds to the second gaze point.

(A12) In some embodiments of at least one of the methods of (A1)-(A11), the method also includes subsequent to receiving the selection command, assigning labels to the first image. The labels include: a) a first label that is based upon the first gaze point; and b) a second label that is based upon the second gaze point. A computer-implemented model used to compute the first gaze point and the second gaze point is updated based upon the first label and the second label (A13) In some embodiments of at least one of the methods of (A1)-(A12), the initiation command is a press of a key of a keyboard, and the selection command is a release of the press of the key of the keyboard.

(A14) In some embodiments of at least one of the methods of (A1)-(A13), the content includes a selectable element, the method further comprising highlighting the selectable element upon detecting that one or more of the first gaze point or the second gaze point corresponds to the selectable element.

(B1) In another aspect, some embodiments include a computer-implemented method performed by a computing system, where the method includes displaying content on a display of the computing system. The method also includes receiving an initiation command, wherein the initiation command indicates that gaze of a user of the computing system is to be employed to set forth input with respect to the content displayed on the display. The method further includes several acts that are performed in response to receiving the content. Such acts include computing a first gaze point based upon a first image generated by the camera, wherein the first gaze point corresponds to a first position in the content at which the user is estimated to be directing their gaze at a first time. The acts also include zooming in on the content based upon the first gaze point to cause a portion of the content corresponding to the first position to be enlarged on the display. The acts additionally include computing a second gaze point based upon a second image generated by the camera, where the second image is generated by the camera subsequent to the first image being generated by the camera, and further where the second gaze point corresponds to a second position in the content at which the user is estimated to be directing their gaze at a second time that is subsequent to the first time. The method additionally includes receiving a selection command, wherein the selection command indicates that a computing operation is to be performed by the computing system with respect to the second position in the content. The method further includes performing the computing operation.

(B2) In some embodiments of the method of (B1), the computing system is a mobile telephone or laptop.

(B3) In some embodiments of at least one of the methods of (B1)-(B2), the method also includes assigning labels to the first image subsequent to receiving the selection command, wherein the labels include: a) a first label corresponding to the first gaze point; and b) a second label corresponding to the second gaze point. A computer-implemented model that computes gaze points is updated based upon the first label and the second label.

(B4) In some embodiments of at least one of the methods of (B1)-(B3), the initiation command is a press of a key of a keyboard, and further wherein the selection command is release of the press of the key of the keyboard.

(B5) In some embodiments of at least one of the methods of (B1)-(B4), the portion of the content includes a hyperlink, and further wherein performing the computing operation comprises selecting the hyperlink.

(C1) In yet another aspect, some embodiments include a computing system that includes a processor, a display operably coupled to the processor, a camera operably coupled to the processor, and memory storing instructions that, when executed by the processor, cause the processor to perform any of the methods disclosed herein (e.g., any of the methods of (A1)-(A14) or (B1)-(B5)).

(D1) In still yet another aspect, some embodiments include a computer-readable storage medium that has instructions stored thereon that, when executed by a processor, cause the processor to perform any of the methods disclosed herein (e.g., any of the methods of (A1)-(A14) or (B1)-(B5)).

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a web site, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A computer-implemented method performed by at least one processor of a computing system, the method comprising:
    receiving an initiation command, the initiation command indicating that the computing system is to receive input from a user of the computing system with respect to content displayed on a display of the computing system based upon a gaze of the user;
    based upon receipt of the initiation command:
        computing a first gaze point based upon a first image of the user generated by a camera of the computing system, wherein the first gaze point corresponds to a first position in the content where the gaze of the user is computed to intersect with the display;
        zooming in on a portion of the content displayed on the display based upon the first gaze point;
        subsequent to zooming in on the portion of the content, computing a second gaze point based upon a second image of the user generated by the camera, wherein the second gaze point corresponds to a second position in the content where the gaze of the user is computed to intersect with the display;
        zooming out from the content based upon the second gaze point, where the content is zoomed out from based upon a distance between the first gaze point and the second gaze point and
        subsequent to zooming out from the portion of the content, computing a third gaze point based upon a third image of the user generated by the camera of the computing system, wherein the third image of the user was generated by the camera subsequent to the second image being generated by the camera, and further wherein the third gaze point corresponds to a third position in the content where the gaze of the user is computed to intersect with the display; and
    subsequent to receiving the initiation command, receiving a selection command, wherein the selection command indicates that a computing operation is to be performed with respect to the third position in the content, and further wherein the computing operation is performed in response to receipt of the selection command.

2. The method of claim 1, wherein the first gaze point is displaced from a center of the display, the method further comprising:
    while zooming in on the portion of the content displayed on the display, panning the content based upon the first gaze point, wherein the content is panned such that the first position in the content is moved towards the center of the display.

3. The method of claim 1, further comprising:
    computing a sequence of gaze points based upon a sequence of images generated by the camera, wherein the sequence of gaze points is computed subsequent to the first gaze point being computed and prior to the second gaze point being computed, wherein zooming in on the content is based upon the sequence of gaze points.

4. The method of claim 1, further comprising:
    displaying a graphical object as an overlay on the content, the graphical object is displayed at the first position based upon the first gaze point and is subsequently displayed at the second position based upon the second gaze point.

5. The method of claim 1, wherein the second gaze point is computed based further upon the first gaze point.

6. The method of claim 1, further comprising:
subsequent to zooming in on the portion of the content and prior to computing the second gaze point, computing a fourth gaze point based upon a fourth image generated by the camera, wherein the fourth gaze point corresponds to a fourth position in the content where the gaze of the user is computed to intersect with the display; and
panning the content based upon the fourth gaze point.

7. The method of claim 1, further comprising:
in response to receiving the selection command, providing the third gaze point to an application that is displaying the content, wherein the application performs the computing operation based upon the third gaze point.

8. The method of claim 7, wherein the computing operation is a selection of a graphical object in the content, wherein the graphical object corresponds to the third gaze point.

9. The method of claim 7, wherein the computing operation is placement of a cursor in a text entry field in the content, wherein the text entry field corresponds to the third gaze point.

10. The method of claim 1, further comprising:
subsequent to receiving the selection command, assigning labels to the first image, wherein the labels comprise:
a first label that is based upon the first gaze point; and
a second label that is based upon the third gaze point,
wherein a computer-implemented model used to compute the first gaze point, the second gaze point, and the second gaze point is updated based upon the first label and the second label.

11. The method of claim 1, wherein the initiation command is a press of a key of a keyboard, and further wherein the selection command is a release of the press of the key of the keyboard.

12. The method of claim 1, wherein the content includes a selectable element, the method further comprising highlighting the selectable element upon detecting that one or more of the first gaze point or the third gaze point corresponds to the selectable element.

13. A computing system comprising:
a processor;
a display operably coupled to the processor;
a camera operably coupled to the processor; and
memory storing instructions that, when executed by the processor, cause the processor to perform acts comprising:
displaying content on the display of the computing system;
receiving an initiation command, wherein the initiation command indicates that gaze of a user of the computing system is to be employed to set forth input with respect to the content displayed on the display;
in response to receipt of the initiation command:
computing a first gaze point based upon a first image generated by the camera, wherein the first gaze point corresponds to a first position in the content at which the user is estimated to be directing their gaze at a first time;
zooming in on the content based upon the first gaze point to cause a portion of the content corresponding to the first position to be enlarged on the display; and
computing a second gaze point based upon a second image generated by the camera, wherein the second image is generated by the camera subsequent to the first image being generated by the camera, and further wherein the second gaze point corresponds to a second position in the content at which the user is estimated to be directing their gaze at a second time that is subsequent to the first time;
receiving a selection command, wherein the selection command indicates that a computing operation is to be performed by the computing system with respect to the second position in the content;
performing the computing operation; and
assigning labels to the first image subsequent to receiving the selection command, wherein the labels comprise:
a first label corresponding to the first gaze point and
a second label corresponding to the second gaze point,
wherein a computer-implemented model that computes gaze points is updated based upon the first label and the second label.

14. The computing system of claim 13 being one of a mobile telephone or a laptop.

15. The computing system of claim 13, wherein the initiation command is a press of a key of a keyboard, and further wherein the selection command is release of the press of the key of the keyboard.

16. The computing system of claim 13, wherein the portion of the content includes a hyperlink, and further wherein performing the computing operation comprises selecting the hyperlink.

17. A computer-readable storage medium comprising instructions that, when executed by a processor, causes the processor to perform acts comprising:
receiving an initiation command, the initiation command indicating that the computing system is to receive input from a user of the computing system with respect to content displayed on a display of the computing system based upon gaze of the user;
based upon receipt of the initiation command:
computing a first gaze point based upon a first image of the user generated by a camera of the computing system, wherein the first gaze point corresponds to a first position in the content where the gaze of the user is computed to intersect with the display;
zooming in on a portion of the content displayed on the display based upon the first gaze point;
subsequent to zooming in on the portion of the content, computing a second gaze point based upon a second image of the user generated by the camera, where the second gaze point corresponds to a second position in the content where the gaze of the user is computed to intersect with the display;
zooming out from the content based upon the second gaze point, where the content is zoomed out from based upon a distance between the first gaze point and the second gaze point; and
subsequent to zooming out from the portion of the content, computing a third gaze point based upon a third image of the user generated by the camera of the computing system, wherein the third image of the user was generated by the camera subsequent to the second image being generated by the camera, and further wherein the third gaze point corresponds to a third position in the content where the gaze of the user is computed to intersect with the display; and
subsequent to receiving the initiation command, receiving a selection command, wherein the selection command indicates that a computing operation is to be performed with respect to the third position in the content, and further wherein the computing operation is performed in response to receipt of the selection command.

18. The computer-readable storage medium of claim 17, wherein the first gaze point is displaced from a center of the display, the acts further comprising:

while zooming in on the portion of the content displayed on the display, panning the content based upon the first gaze point, wherein the content is panned such that the first position in the content is moved towards the center of the display.

19. The computer-readable storage medium of claim 17, the acts further comprising:

computing a sequence of gaze points based upon a sequence of images generated by the camera, wherein the sequence of gaze points is computed subsequent to the first gaze point being computed and prior to the second gaze point being computed, wherein zooming in on the content is based upon the sequence of gaze points.

20. The computer-readable storage medium of claim 17, wherein the content includes a selectable element, the method further comprising highlighting the selectable element upon detecting that one or more of the first gaze point, the second gaze point, or the third gaze point corresponds to the selectable element.

* * * * *